United States Patent
Crippen et al.

(10) Patent No.: US 6,827,932 B2
(45) Date of Patent: Dec. 7, 2004

(54) ACTIVATED CHARCOAL BASED COMPOSITION AND METHOD FOR REDUCING HANGOVER SYMPTOMS ASSOCIATED WITH THE CONSUMPTION OF ALCOHOL CONTAINING BEVERAGES

(76) Inventors: Raymond Crippen, 4601 Hampton Rd. at 8800 Walther Blvd., Baltimore, MD (US) 21234; Manoj Bhargava, 6250 Royal Pointe Rd., West Bloomfield, MI (US) 48322; Thomas F. Morse, 336 Wolverine Dr., Walled Lake, MI (US) 48390

( * ) Notice: Subject to any disclaimer, the term of this patent is extended or adjusted under 35 U.S.C. 154(b) by 0 days.

(21) Appl. No.: 10/042,283

(22) Filed: Jan. 11, 2002

(65) Prior Publication Data

US 2002/0155103 A1 Oct. 24, 2002

Related U.S. Application Data

(60) Provisional application No. 60/260,916, filed on Jan. 12, 2001.

(51) Int. Cl.[7] .......................... A61K 33/44; A61K 33/10; B01J 21/18
(52) U.S. Cl. ........................ 424/125; 424/687; 502/180; 502/416; 502/417
(58) Field of Search ....................... 210/323.1; 502/180, 502/184, 416, 417; 514/220, 811, 922, 974; 424/125, 687, 715, 464, 451, 722, 725.1, 489; 252/183.13

(56) References Cited

U.S. PATENT DOCUMENTS

| | | | | |
|---|---|---|---|---|
| 3,934,007 A | * | 1/1976 | Gussin et al. | 424/125 |
| 4,122,169 A | * | 10/1978 | Geils | 424/125 |
| 4,242,226 A | * | 12/1980 | Siren | 252/422 |
| 4,594,249 A | * | 6/1986 | Procter et al. | 424/125 |
| 5,225,510 A | * | 7/1993 | Bank et al. | 528/12 |
| 5,885,599 A | * | 3/1999 | Peterson et al. | 424/405 |
| 6,485,758 B2 | * | 11/2002 | Mirza et al. | 424/725 |
| 2003/0007962 A1 | * | 1/2003 | Vergez et al. | 424/94.21 |

FOREIGN PATENT DOCUMENTS

JP 04-096993 * 3/1992 ........... C09K/17/00

OTHER PUBLICATIONS

Grant et al., Grant & Hackh's Chemical Dictionary, p. 111, McGraw–Hill, inc., New York, May 1994.*
Sport–Horse Supreme, Agriculture Canad Reg. # 820295 (1984).*
Chaser, Dec. 2001, Living Essentials.*

* cited by examiner

*Primary Examiner*—Patricia Leith
(74) *Attorney, Agent, or Firm*—Pillsbury Winthrop LLP

(57) ABSTRACT

The invention provides a composition which is effective in the prevention or delay of the onset of side effects associated with alcohol consumption or the reduction or alleviation of those effects. The composition of the invention includes activated charcoal and limestone, optionally activated limestone. Optionally, the composition of the invention also includes vitamin B1 and/or other agents such as fatigue relieving agents. Preferably, the composition of the invention is provided in the form of tablets or powder encapsulated in a gelatin capsule. The composition of the invention is provided in pre-dosed quantities varying from between about 100 and 500 milligrams per dose. The invention also provides a method of reducing or alleviating the deleterious effects associated with alcohol consumption. The method includes administration, preferably multiple administration at regularly spaced intervals before, during, and after alcohol consumption of a composition containing activated charcoal and activated limestone.

43 Claims, No Drawings

ACTIVATED CHARCOAL BASED COMPOSITION AND METHOD FOR REDUCING HANGOVER SYMPTOMS ASSOCIATED WITH THE CONSUMPTION OF ALCOHOL CONTAINING BEVERAGES

CROSS-REFERENCE TO RELATED APPLICATIONS

This application claims the benefit of U.S. provisional application No. 60/260,916, filed on Jan. 12, 2001, which is hereby incorporated in its entirety by reference.

FIELD OF THE INVENTION

The present invention relates to a composition which is effective in reducing the effects associated with alcohol consumption and to a method based on administering the composition to a subject in need thereof.

BACKGROUND OF THE INVENTION

As long as history has been recorded, every society has used substances that alter mood, thought and feeling. Alcohol based beverages have played a central role throughout modem history as a prominent ingredient in social and cultural gatherings. The association of alcohol based beverages with culinary enjoyment and other human celebrations have been central to the development of western culture. The role of alcohol based beverages in social human activities is increasingly spreading throughout the globe due to the adoption by populations around the world of the western lifestyle and cultural standards.

However, while consumption of alcohol based beverages in moderation has been associated with refined and sophisticated western lifestyle, abuse of alcohol and alcohol dependency (i.e., alcoholism) are increasingly a public health problem for the modern western society, and now worldwide. In the United States alone, an estimated 13 million adults exhibit symptoms of alcohol dependency due to excessive alcohol intake, and an additional 7 million abuse alcohol without showing symptoms of dependency.

Alcohol dependency and abuse are very expensive in economic and medical terms. It is estimated that alcohol abuse related expenditures will cost the U.S. well over 2 hundred billion dollars in the next year with no prospect of falling or leveling off. The social and psychological damages inflicted on individuals as consequence of alcohol abuse, for example, as more children are born with fetal alcohol syndrome and more victims fall to alcohol related accidents, homicides, suicides, etc. are immense. In view of the staggering statistics associated with alcohol abuse, most, if not all efforts concerned with the effects of alcohol focused on the treatment of alcohol abuse and alcoholism. While those efforts are important and should be pursued, they should not overshadow the importance of the positive effects of moderate consumption of alcohol within ancestral social and cultural norms.

The less dramatic effects of alcohol when consumed in moderation have received little or no interest. There have been very few remedies rationally developed for addressing the effects of moderate alcohol consumption. Those effects include alcohol related "hangover" which is generally characterized by a headache, tremulousness, nausea, sour stomach, diarrhea, fatigue and decreased cognitive or visual-spatial skills.

The symptoms referred to as hangover are believed to be connected to dehydration, hormonal alterations, de-regulation of cytokine pathways and other toxic effects of alcohol. Dehydration is believed to be one of the primary causes of hangover. As alcohol is ingested, ethanol is introduced into the blood stream. In the body, alcohol and its metabolites are identified as toxins and are therefore broken down to less harmful chemical entities. In the body, the liver and kidneys are the organs where most of toxin processing takes place. In order for toxins to be processed adequately by the liver and kidneys, they must be dissolved in water. When the amount of toxins generated by alcohol consumption is higher than the amount of water available in the stomach, water is drawn from other areas of the body where water may be available. In order to process excessive amounts of toxins associated with alcohol consumption, water is generally drawn from the blood, the lymphnodes and the brain. Intensive use of the water available in the body in the processing of toxins results in dehydration, which in turn may result in effects ranging from mere headaches to serious harm to the brain, kidneys, liver, lymphnodes and other vital parts of the human body.

Other effects of alcohol consumption are associated with the presence of congeners generated during the preparation of alcohol beverages, particularly in fermentation processes. Another source for the effects of alcohol consumption is associated with the build up of acetaldehyde during the metabolism of alcohol by the liver kidneys. Alcohol breakdown in the liver involves two steps which are catalyzed by two different enzymes. In the first step, the enzyme alcohol dehyrogenase (ADH) converts alcohol into extremely toxic acetaldehyde. In the second step, the enzyme dehyrogenease (ALDH) converts the acetaldehyde into harmless acetate.

When acetaldehyde is produced at a faster rate than it is converted to acetate, excess acetaldehyde accumulates in the liver which produces an extreme visible reaction. The visible violent effects of acetaldehyde accumulation on the body has resulted in particular attention to the treatment of symptoms associated with acetaldehyde accumulation in the liver. Most studies have focused on using vitamin B6 to help reduce the amount of acetaldehyde accumulated in the liver due to alcohol ingestion as vitamin B6 is believed to be a co-factor that facilitates the conversion of acetaldehyde by ALDH into acetate. However, it has been shown that vitamin B6 is generally available in sufficient amounts in the body upon consumption of alcohol and therefore the administration of high doses of B6 have not resulted in significant reduction of the side effects of alcohol consumption. However, studies have shown that vitamin B1 required for (ADH) is potentially available in insufficient amounts to both supply the required Thiamine (B1) for the essential oxygen-dependent part of the metabolism of alcohol and supply the required vitamin B I to the body. The net affect is in addition to making it harder to breakdown the alcohol into the harmless acetate for efficient removal from the body, high blood alcohol levels can potentially reduce the vitamin B1 supply to the brain. Long term effects of vitamin B1 deficiency in the brain can cause severe health problems.

Another approach for reducing the undesirable effects of alcohol consumption has focused on the removal of alcohol and its metabolites from the blood stream through absorption by alcohol absorbing materials. Specifically, U.S. Pat. No. 4,594,249, the contents of which are hereby incorporated by referenced in their entirety, discloses the use of activated charcoal in alleviating the effects of consumption of alcohol containing beverages. The '249 patent discloses that the effects of alcohol consumption may be reduced by administering to a subject activated charcoal in amounts varying between 5 and 15 milligrams per kilogram of weight of the subject. However, administration of activated charcoal alone has provided only limited reduction of the hangover symptoms associated with alcohol consumption. More effective reduction of those effects would necessitate the injection of substantially larger quantities of activated charcoal.

The effective use of activated charcoal in the treatment of the effects of alcohol consumption may require the administration of high doses in the range of 50 grams or more which must be provided in water suspension form. However, charcoal suspension adheres to the mucosal surfaces of the throat, and gives a chalk like taste which is objectionable and may reduce the desirability of intake of activated charcoal. The limited effectiveness of activated charcoal at doses that are adequate for administration in tablet or capsule form essentially has resulted in a halt in the efforts to develop methods of reducing the effects of alcohol consumption based on activated charcoal.

Thus, there remains a need for compositions and methods based on activated charcoal, yet presenting a significantly enhanced effect in reducing the hangover symptoms associated with alcohol consumption without the need for increased doses of activated charcoal to be administered to a subject beyond the quantities adequate for capsule and tablet packaging. It is therefore an object of the present invention to provide a composition which is based on activated charcoal and which allows a significant reduction in the effects of alcohol consumption while administrating activated charcoal in small doses which are compatible with tablet and capsule packaging and administration.

SUMMARY OF THE INVENTION

The present invention is based on the unexpected discovery that the combination of activated charcoal with limestone, optionally activated limestone allows for the preparation of a composition which is significantly more effective in reducing the effects of alcohol consumption and which allows administration of activated charcoal in doses that are compatible with the preparation of the composition in tablet or capsule form.

Thus, in its broadest embodiment, the present invention provides a composition for the prevention or delay of the on set of the side effects associated with alcohol consumption or the reduction or alleviation of said side effects, wherein said composition comprises activated charcoal and limestone, optionally activated limestone. Optionally, the composition may further include vitamin B1. Typically, the composition will comprise up to 80 wt. % activated charcoal, for instance more than 20 wt. % and preferably between 30 and 60 wt. % and more preferably up to 45 wt. % activated charcoal. The composition may also include up to 80 wt. % activated limestone, for instance 20 wt. %, 40 wt. % or 60 wt. % and preferably the activated limestone will be present in the composition in a range between 55 wt. % and 75 wt. %. and more preferably between 40 and 70 wt. %.

Other components with beneficial effects in reducing the side effects of alcohol consumption that may be included in the composition of the invention include rehydratings agents, agents capable of reducing alcohol dependency, such as olanzapine, fatigue relieving agents, such as L-methionine or a biologically acceptable salt thereof, or a biologically acceptable magnesium salt, folic acid, vitamin B12 or mixture thereof.

In a second embodiment, the invention provides a method for alleviating the undesirable "hangover" effects associated with alcohol ingestion comprising administering to a subject a composition comprising activated charcoal and limestone, optionally activated limestone.

DETAILED DESCRIPTION OF PREFERRED EMBODIMENTS OF THE INVENTION

The present invention is based on the unexpected discovery that a composition comprising activated charcoal and limestone, optionally activated limestone allows for more effective and faster alleviation and reduction of the effects of alcohol ingestion compared to administering a composition based on activated charcoal alone. The enhanced activity of the composition of the invention allows for the preparation of activated charcoal based compositions in the form of tablets or capsules containing the composition in the form of powder. In particular, the invention is based on the discovery that activated charcoal and activated limestone synergistically combine to significantly reduce the presence of alcohol or its harmful metabolites in the blood stream.

It is believed that the combination of activated charcoal and limestone, optionally activated limestone allows for significantly enhancing the adsorption properties of the composition of the invention. In significantly increasing the efficacy of the composition of the invention while using activated charcoal in a quantity of between 5 to 15 milligrams per kilogram of body weight allows for the formulation of the composition of the invention in acceptable forms, such as tablet form and encapsulated powder. In effect, with the addition of limestone, optionally activated limestone, compositions based on activated charcoal are now much more desirable in the alleviation of the symptoms associated with alcohol ingestion. Recognizing that the composition may be incorporated into a variety of delivery systems, the active ingredients, i.e., the activated charcoal and the activated limestone, can be present in amounts of between 20 and 80 wt. % activated charcoal (correspondingly between 20 and 80 wt. % activated limestone), preferably 30 and 50 wt. % activated charcoal with the balance activated limestone.

Activated charcoal is a fine, black, insoluble powder, without taste or odor. After preparation by combustion of organic material such as wood, it is activated by an oxidizing gas flow at high temperature. This process creates a solid having an internal network of pores presenting an internal surface area which is much larger than the external surface area of the solid. For example, the total surface area of activated charcoal is on the order of 1,000 meters per gram while the total full volume is about 1 cubic centimeter per gram. Activated charcoal is commercially available in many different grades and under a variety of brand names.

In conjunction with activated charcoal, the composition of the invention also comprises limestone, optionally activated limestone. Limestone is a sedimentary rock composed mainly of calcium carbonate ($CaCO_3$), usually in the form of calcite or aragonite. Limestone may contain considerable amounts of magnesium carbonate (dolomite) as well; minor constituents also commonly present include clay, iron carbonate, feldspar, pyrite, and quartz. Most limestones have a granular texture. Their constituent grains range in size from 0.001 mm (0.00004 inch) to visible particles. In many cases, the grains are microscopic fragments of fossil animal shells. Limestone has two origins: (1) biogenic precipitation from sea water (autochthonous limestone), the primary agents being lime-secreting organisms and foraminifera; and (2) mechanical transport and deposition of preexisting limestones (allochthonous limestone), forming clastic deposits.

Limestone has long fascinated earth scientists because of its rich fossil content. Limestone is commercially available from various sources, including Prime PVC Inc.

Although compositions according to the invention may be administered to subjects in a variety of forms, they are preferably given in the form of loose powder encapsulated in a water soluble encapsulating material. Capsules may contain convenient dosage quantities in the range from 100 to 800 milligrams, preferably 100 to 500 milligrams, per capsule. Compositions of the invention may also be administered in tablet form preferably in dose sizes of from about 50 to 300 milligrams per tablet. The effect of combining activated charcoal with limestone, optionally activated limestone according to the invention may also be achieved by administering two types of tablets or capsules, one type of tablet or capsule containing activated charcoal and the other type of tablet or capsule containing limestone or activated limestone.

Compositions according to the invention including activated charcoal and limestone, optionally activated limestone, and optionally other ingredients such as Vitamin B1, can be prepared according to various methods. Particularly, the composition of the invention can be prepared according to the method disclosed in U.S. Pat. No. 5,496,566, the contents of which are hereby incorporated by reference in their entirety.

For the effective alleviation of the adverse side effects of alcohol ingestion, the composition of the invention is preferably packaged in pre-dosed quantities and in a form suitable for self-administration. Preferably, a first dose, in the form of a tablet or capsule containing the composition of the invention is taken by a subject shortly before or at the time of beginning to drink an alcoholic beverage. The pre-dosed tablet or capsule preferably contains between about 5 and 15 milligrams of the composition of the invention per kilogram of body weight. For example, a standard dose of the composition of the invention may contain two tablets or capsules each containing 300 to 600 milligrams, preferably 400 milligrams, of the composition of the invention.

Optimum effects of the composition of the invention in reducing or preventing the onset of the deleterious effects associated with alcohol ingestion includes self-administration of one dose of the composition of the invention in intervals of one to three hours during moderate alcohol consumption or one to two hours during heavy drinking. When alcohol is consumed, it is ingested into the digestive tract and is quickly absorbed into the circulatory system. The administration of a dose of a composition of the invention including activated charcoal and limestone (preferably activated limestone), and optionally, vitamin B1 during alcohol consumption reduces but does not totally eliminate the absorption of alcohol into the bloodstream. Thus, the more desirable effects associated with alcohol consumption such as the feeling of euphoria associated with the presence of alcohol and its metabolites in the bloodstream is still maintained while the deleterious effects associated with an excessive presence of alcohol or its metabolites in the bloodstream are significantly reduced or eliminated. Excessive amounts of alcohol and/or its metabolites are absorbed by the activated charcoal and activated limestone of the composition of the invention while the optional other components help reduce the effects of alcohol and its metabolites through mechanisms other than the absorption or adsorption of alcohol or its metabolites.

It is highly desirable to administer one or few final doses of the composition of the invention at the end of the period of alcohol consumption. The composition administered after alcohol intake is terminated helps clear ethanol and its metabolites from the circulatory system. It is believed that the adsorption by the composition of the invention of alcohol, its metabolites, and congeners associated with its production, produces a gradient of concentration of these undesirable components in favor of movement of the compounds back into the gut. Therefore, the quantity of alcohol, its metabolites and congeners present in the bloodstream is significantly reduced which in turn results in significant reduction in the deleterious effects associated with alcohol consumption, particularly those known to be associated with the "hangover" effect.

EXAMPLES

In order to show the efficacy of the composition of the invention in significantly reducing blood alcohol levels upon the ingestion of alcohol based beverages, the composition of the invention was administered to a group of volunteers who were provided with alcohol beverages and subjected to blood alcohol analysis through breathalyzer measurements. The first group (subjects A–D) consisted of 4 females who were provided with various alcohol beverages and two capsules containing about 850 milligrams of a composition containing activated charcoal and activated limestone according to one embodiment of the invention, which were orally self-administered with the second drink. The second group (subjects E and F) consisted of two males, each took two capsules, each containing 900 milligrams of the composition of the invention immediately after the last drink. The characteristics of the volunteers and the results obtained during this experiment are summarized in Tables 1–3.

TABLE 1

| Subject | Age | Weight | Height | Gender | Time of last meal | Time Subject began drinking |
|---------|-----|--------|--------|--------|-------------------|-----------------------------|
| A | 35 | 160 | 5'7" | F | 8:00 am | 5:30 pm |
| B | 36 | 128 | — | F | 3:30 pm | 5:30 pm |
| C | 35 | 120 | — | F | 3:30 pm | 5:30 pm |
| D | 37 | 122 | — | F | 2:00 pm | 4:00 pm |
| E | 47 | 165 | — | M | 12:30 pm | 2:30 pm |
| F | 31 | 170 | — | M | 12:30 pm | 2:30 pm |

TABLE 2

| Subject | Time Subject began drinking | Type of Drink consumed | Time Subject stopped drinking | No. of Drinks consumed |
|---------|------------------------------|------------------------|-------------------------------|------------------------|
| A | 5:30 pm | Hurricanes - dark and light rum | 9:30 pm | 9 |
| B | 5:30 pm | Rum | 9:30 pm | 6 |
| C | 5:30 pm | Tequila | 9:30 pm | 3 |
| D | 4:00 pm | Beer and rum | 9:30 pm | 10 |
| E | 2:30 pm | Beer | 4:35 pm | 6 |
| F | 2:30 pm | Beer | 4:35 pm | 6 |

TABLE 3

BREATHALYZER READING

| Subject | at middle of drinking session | after 20 min. of last drink | After 50 min. of last drink | after 1 hr. of last drink | after 1 hr. and 15 min. of last drink | after 1 hr. and 30 min. of last drink |
|---------|---|---|---|---|---|---|
| A | .11 | .7 | .04 | .03 | .02 | .00 |
| B | .4 | .2 | .00 | — | — | — |
| C | .3 | .2 | .00 | — | — | — |
| D | .19 | .15 | .09 | .05 | .03 | .02 |
| E* | — | .15 | .17 | .15 | .14 | .12 |
| F** | — | .09 | .12 | .1 | .09 | .08 |

*The last reading for subject E was conducted 2 hours and 30 minutes of last drink and indicated a blood alcohol level of 0.13.
**The blood alcohol level for subject F decreased to 0.06 after 2 hours and 30 minutes of last drink and to 0.03 after 4 hours and 15 minutes of last drink.

The results shown in Table 3 show that the composition of the invention is highly effective when taken during the course of drinking session compared to taking the composition at the end of the drinking session. Results similar to those obtained with the subjects who took the composition of the invention during the drinking session would be obtained if the composition is administered prior to the start of the drinking session. However, when the composition is taken before the start of the drinking session the effect of alcohol is drastically reduced and the subject may not experience the euphoria associated with the drinking of alcoholic beverages. Thus, in a preferred embodiment the composition of the invention is administered shortly after the start of the drinking session (after the first drink), to keep the blood alcohol level low while at the same time allowing the subject to experience some of the euphoria and nice feeling associated with moderate alcohol consumption.

In order to test[1] the efficacy of the composition in reducing or eliminating hangover-related symptoms a randomized, blind, placebo-controlled trial was implemented on nine male and female subjects.

Initially, 10 subjects entered the test protocol, 1 was disqualified because the subject did not show any reaction to alcohol consumption. The remaining 9 subjects participated in four evening sessions, as set forth in Table 4, conducted in random order. The drinks consumed approximately every half hour consisted of domestic wine (approximately 13.5 to 14% of alcohol by volume) in an volume/subject's body weight equal to approximately 0.25 g alcohol/kg of body weight (a total of 1 g alcohol/kg of body weight was administered over a 2 hour period) and dosage administered, as indicated in Table 4, during the session equals 2 capsules (450 milligrams capsules comprising approximately 35 wt. % activated charcoal and approximately 65 wt. % activated limestone).

TABLE 4

| Session Sequence | 1st Drink | 2nd Drink | 3rd Drink | 4th Drink | Final Dosage |
|---|---|---|---|---|---|
| A | P-dosage | — | P-Dosage | — | P-Dosage |
| B | TC-Dosage | — | P-Dosage | — | P-Dosage |
| C | P-dosage | — | TC-Dosage | — | P-Dosage |
| D | TC-dosage | — | P-Dosage | — | TC-Dosage |

Table Notes:
TC => Test Composition
P => Placebo

Measurements were performed based on subjective symptom scores for headache, fatigue, dry mouth, diarrhea, anorexia, nausea, tremulousness and sense of overall well being were recorded the morning after the session (between 8:30 and 9:30 am). In almost all cases, the severity of the symptoms was reduced. Table 5 summarizes the results based on the data collected for the double dosage session (sequence D) vs. the placebo session (sequence A). e.

TABLE 5

|  | Average Placebo Score | Average Double Dosage Score |
|---|---|---|
| Headache | 2 | 1.4 |
| Fatigue | 3 | 1.6 |
| Dry mouth | 3.4 | 2 |
| Diarrhea | 1.3 | 1 |
| Anorexia | 1.3 | 1.3 |
| Nausea | 1.6 | 1.3 |
| Tremulousness | 1.3 | 1.1 |
| Well being** | 3.2 | 4.6 |

1 = Best (no symptoms) and 5 = Worst (severe symptoms)
*5 = Best and 1 = Worst

From the above reported results, it can be concluded that administration of the activated calcium carbonate/charcoal was associated with significant reduction in severity of most alcohol-related hangover symptoms in those who are subject to hangovers.

While the present invention has been described in illustrative terms, the scope thereof is only limited by the claims which follow.

What is claimed is:

1. A composition for the prevention or delay of the onset of side effects associated with alcohol consumption or the reduction or alleviation of said side effects, wherein said composition comprises activated charcoal and limestone, the activated charcoal being present in the composition between 20–80% by weight.

2. A capsule comprising the composition of claim 1.

3. The capsule of claim 2 comprising between about 100 and 500 milligrams of said composition.

4. The capsule of claim 2 wherein said composition comprises between 30 and 60 weight % of activated charcoal and between 40 and 70 weight % of limestone.

5. The capsule of claim 2 further comprising a re-hydrating agent.

6. The capsule of claim 2 further comprising an agent capable of enhancing aldehyde dehydrogenase activity.

7. The capsule of claim 6 wherein said agent is vitamin B1.

8. The capsule of claim 2 further comprising a fatigue relieving agent.

9. The capsule of claim 8 wherein said fatigue relieving agent is vitamin B12.

10. The capsule of claim 2 further comprising an agent capable of reducing alcohol dependency.

11. The capsule of claim 10 wherein said agent capable of reducing alcohol dependency is olanzapine.

12. A tablet comprising the composition of claim 1.

13. The tablet of claim 12 comprising from about 100 to about 500 milligrams of said composition.

14. The tablet of claim 12 wherein said composition comprises between 30 and 60 weight % of activated charcoal and between 40 and 70 weight % of limestone.

15. The tablet of claim 12 further comprising a re-hydrating agent.

16. The tablet of claim 12 further comprising an agent capable of reducing alcohol dependency.

17. The tablet of claim 16 wherein said agent capable of reducing alcohol dependency is olanzapine.

18. The tablet of claim 12 further comprising an agent capable of enhancing aldehyde dehydrogenase activity.

19. The tablet of claim 18 wherein said agent is vitamin B1.

20. The tablet of claim 12 further comprising a fatigue relieving agent.

21. The tablet of claim 20 wherein said fatigue relieving agent is vitamin B12.

22. A method of alleviating the deleterious effects of alcohol consumption comprising administering to a person in need thereof, the capsule of claim 2.

23. The method of claim 22 wherein said capsule comprises between bout 100 and 500 milligrams of said composition.

24. The method of claim 22 wherein said capsule comprises between 30 and 60 weight % of activated charcoal and between 40 and 70 weight % of limestone.

25. The method of claim 22 wherein said capsule further comprises a re-hydrating agent.

26. The method of claim 22 wherein said capsule further comprises agent capable of reducing alcohol dependency.

27. The method of claim 22 wherein said capsule further comprises olanzapine.

28. The method of claim 22 wherein said capsule further comprises agent capable of enhancing aldehyde dehydrogenase activity.

29. The method of claim 28 wherein said agent is vitamin B1.

30. The method of claim 22 wherein said capsule further comprises fatigue relieving agent.

31. The method of claim 30 wherein said fatigue relieving agent is vitamin B12.

32. A method of alleviating the deleterious effects of alcohol consumption comprising administering to a person in in need thereof, the tablet of claim 12.

33. The method of claim 32 wherein said tablet comprises between about 100 and 500 milligrams of said composition.

34. The method of claim 32 wherein said tablet comprises between 30 and 60 weight % of activated charcoal and between 40 and 70 weight % of limestone.

35. The capsule of claim 34 wherein said composition is present between about 100 and 800 milligrams.

36. The method of claim 32 wherein said tablet further comprises a re-hydrating agent.

37. The tablet of claim 36 wherein said composition is present between about 100 and 800 milligrams.

38. The method of claim 32 wherein said tablet further comprises agent capable of reducing alcohol dependency.

39. The method of claim 32 wherein said tablet further comprises olanzapine.

40. The method of claim 32 wherein said tablet further comprises an agent capable of enhancing aldehyde dehydrognease activity.

41. The method of claim 40 wherein said agent is vitamin 1.

42. The method of claim 32 wherein said tablet further comprises a fatigue relieving agent.

43. The method of claim 32 wherein said fatigue relieving agent is vitamin B12.

* * * * *

UNITED STATES PATENT AND TRADEMARK OFFICE
CERTIFICATE OF CORRECTION

PATENT NO. : 6,827,932 B2
DATED : December 7, 2004
INVENTOR(S) : Raymond L. Crippen et al.

It is certified that error appears in the above-identified patent and that said Letters Patent is hereby corrected as shown below:

Column 9,
Line 29, replace "between bout 100" with -- between about 100 --.

Column 10,
Line 12, replace "in in need thereof" with -- in need thereof --.
Line 29, replace "dehy-drognease activity." with -- dehy-drogenase activity. --.
Line 31, replace "vitamin 1." with -- vitamin B1. --.

Signed and Sealed this

First Day of March, 2005

JON W. DUDAS
*Director of the United States Patent and Trademark Office*